United States Patent [19]

Schulz et al.

[11] Patent Number: 5,433,912
[45] Date of Patent: Jul. 18, 1995

[54] PROCESS FOR INJECTION MOLDING ARCUATELY-SHAPED HOLLOW ARTICLES

[75] Inventors: Werner H. Schulz, Cupertino; Horst Kaiser, Fremont; Louis Temesvary, Sunnyvale, all of Calif.

[73] Assignee: Kimberly-Clark Corporation, Neenah, Wis.

[21] Appl. No.: 205,913

[22] Filed: Mar. 3, 1994

[51] Int. Cl.6 .............................................. B29C 45/44
[52] U.S. Cl. .................... 264/297.2; 264/318; 264/328.8; 264/334; 425/577; 425/DIG. 58
[58] Field of Search ............... 264/297.2, 328.1, 328.8, 264/328.14, 328.16, 318, 334; 425/577, 589, 592, 418, 441, 442, 451.3, 451.4, 451.5, 468, DIG. 10, DIG. 58, DIG. 247; 249/144

[56] References Cited

U.S. PATENT DOCUMENTS

| | | |
|---|---|---|
| 3,028,630 | 4/1962 | Walker . |
| 3,049,759 | 8/1962 | Eberhardt .................. 425/DIG. 58 |
| 3,196,873 | 7/1965 | Bletzinger et al. . |
| 3,264,691 | 8/1966 | Whitehead . |
| 3,369,544 | 2/1968 | Crockford . |
| 3,433,225 | 3/1969 | Voss et al. . |
| 3,469,286 | 9/1969 | Crockford . |
| 3,499,447 | 3/1970 | Mattes et al. . |
| 3,608,441 | 9/1971 | Johnson . |
| 3,625,787 | 12/1971 | Radl et al. . |
| 3,643,661 | 2/1972 | Crockford . |
| 3,645,263 | 2/1972 | Bates . |
| 3,683,759 | 8/1972 | Voss et al. . |
| 3,736,903 | 6/1973 | Townsend . |
| 3,737,512 | 6/1973 | Stalter .............................. 264/297.2 |
| 3,746,493 | 7/1973 | Stalter . |
| 3,765,417 | 10/1973 | Crockford . |
| 3,796,407 | 3/1974 | Brown ................................ 425/468 |
| 3,805,786 | 4/1974 | Bernardin et al. . |
| 3,830,236 | 8/1974 | Hanke . |
| 3,882,869 | 5/1975 | Hanke . |
| 3,930,777 | 1/1976 | Ramsey ................................ 425/190 |

(List continued on next page.)

FOREIGN PATENT DOCUMENTS

| | | |
|---|---|---|
| 833201 | 2/1970 | Canada . |
| 882951 | 10/1971 | Canada . |
| 914628 | 11/1972 | Canada . |
| 943703 | 3/1974 | Canada . |
| 945703 | 4/1974 | Canada . |
| 0243250A1 | 10/1987 | European Pat. Off. . |

(List continued on next page.)

*Primary Examiner*—Jill L. Heitbrink
*Attorney, Agent, or Firm*—Thomas J. Connelly

[57] ABSTRACT

A process for injection molding arcuately-shaped hollow articles is disclosed. The process includes the steps of positioning a stack mold into an injection molding machine. The stack mold has first, second and third mold blocks with the first mold block positioned between the second and third mold blocks. Each of the mold blocks has a plurality of cavities formed therein. The cavities formed in the first mold block are designed to mate with the cavities formed in the second and third mold blocks when the stack mold is closed to form a plurality of arcuately-shaped cavities. The stack mold further contains a pair of slide carriers movably connected to each of the second and third mold blocks and a plurality of inner cores secured to each of the slide carriers. The stack mold is closed by first moving both of the pairs of slide carriers such that each of the inner cores is positioned within one of the arcuately-shaped cavities to form a hollow interior in each of the molded articles. The first and second mold blocks are then moved against the third mold block. Molten material is introduced into the arcuately-shaped cavities and is allowed to solidify. The stack mold is opened by moving the first and second movable blocks away from the third mold block and then moving both of the pairs of slide carriers outward to remove the inner cores from the arcuately-shaped cavities. The injection molded articles are then removed from the stack mold.

20 Claims, 4 Drawing Sheets

U.S. PATENT DOCUMENTS

| | | | |
|---|---|---|---|
| 4,050,667 | 9/1977 | Kossett | 249/82 |
| 4,154,566 | 5/1979 | Ward | 425/451.3 |
| 4,184,834 | 1/1980 | Barber | 425/548 |
| 4,274,617 | 6/1981 | Schriever | 425/589 |
| 4,276,881 | 7/1981 | Lilaonitkul . | |
| 4,326,527 | 4/1982 | Wollangk et al. . | |
| 4,543,086 | 9/1985 | Johnson . | |
| 4,650,459 | 3/1987 | Sheldon . | |
| 4,676,773 | 6/1987 | Sheldon . | |
| 4,721,280 | 1/1988 | Barainsky | 249/185 |
| 4,743,237 | 5/1988 | Sweere . | |
| 4,753,413 | 6/1988 | Haigh | 249/64 |
| 4,755,166 | 7/1988 | Olmstead . | |
| 4,765,938 | 8/1988 | Schmidt et al. . | |
| 4,775,377 | 10/1988 | Sweere . | |
| 4,792,326 | 10/1988 | Tews . | |
| 4,856,980 | 8/1989 | Laurita | 425/572 |
| 4,857,044 | 8/1989 | Lennon . | |
| 4,872,933 | 10/1989 | Tews | 156/184 |
| 4,929,167 | 5/1990 | Pepper | 425/325 |
| 5,002,526 | 3/1991 | Herring . | |
| 5,037,597 | 8/1991 | McGinley et al. | 264/297.2 |
| 5,100,435 | 3/1992 | Onwumere . | |
| 5,225,215 | 7/1993 | Syvrud | 425/577 |
| 5,267,953 | 12/1993 | Paul et al. . | |

FOREIGN PATENT DOCUMENTS

| | | |
|---|---|---|
| 46-12911 | 4/1971 | Japan . |
| 46-24546 | 7/1971 | Japan . |
| 53-127559 | 11/1978 | Japan . |
| 1108291 | 4/1968 | United Kingdom . |
| 2202750 | 10/1988 | United Kingdom . |
| 2211097 | 6/1989 | United Kingdom . |

PROCESS FOR INJECTION MOLDING ARCUATELY-SHAPED HOLLOW ARTICLES

FIELD OF THE INVENTION

This invention relates to a process for injection molding arcuately-shaped hollow articles. More specifically, this invention relates to a process for injection molding an arcuately-shaped outer tube which can then be assembled with an inner tube to form a curved tampon applicator.

BACKGROUND OF THE INVENTION

Today, tampon applicators represent a common means used by women to position a catamenial tampon into their vaginas. Many such applicators consist of two hollow, cylindrical tubes telescopically attached together. Such tampon applicators include an outer tube which contains a tampon and an inner tube which is used to expel the tampon from the outer tube. The applicator can be constructed of various materials including paper, cardboard, coated paper or plastic.

Up until now, the outer tubes of such tampon applicators have been manufactured having a straight cylindrical axis. This is especially true for outer tubes which are injection molded from synthetic or thermoplastic resins. One reason for this is that it is extremely difficult to engineer, design and build a mold that can produce an arcuately-shaped article having a hollow interior. Such molds are also very expensive to build and maintain. It is a challenge to design a mold which is capable of inserting and withdrawing an inner core into and out of an arcuately-shaped cavity without destroying the molded article. One approach is to construct a mold using a multitude of movable parts. However, the fit between two adjacent parts creates an area into which molten material can flow. When the surfaces of the two adjacent parts are not machined to a close tolerance, molten material can flow into such areas and create flash lines on the exterior surface of the finished article. Such flash lines are unacceptable and the article has to be discarded.

Another problem with injection molding arcuately-shaped hollow articles is that it is extremely difficult to mold such articles at high speeds needed for commercial operations. Unlike an extrusion molding process, injection molding is a batch operation which is dependent upon cycle time. A complete cycle includes closing the mold, introducing molten material, cooling the material so that it solidifies to form an article, opening the mold and then removing the finished article. As the cycle time increases, the number of articles which can be molded per minute decreases. One is also limited by the size of the mold. Large molds having more than 64 cavities are difficult to build and operate. Such large molds also require an injection molding machine that can deliver extremely high closing pressures and require complex controls for maintaining an even distribution of temperature across the entire surface of the mold. If a mold is operated with temperature variations between the cavities, certain cavities will not be capable of forming a complete article and this will result in increased waste. Because of the above-identified problems, no one has introduced an arcuately-shaped tampon applicator into the market place which has been injection molded.

Now a process has been invented for injection molding arcuately-shaped hollow articles at commercial speeds in an efficient manner and at a relatively low cost.

SUMMARY OF THE INVENTION

Briefly, this invention relates to a process for injection molding arcuately-shaped hollow articles. The process includes the steps of positioning a stack mold into an injection molding machine. The stack mold has first, second and third mold blocks with the first mold block positioned between the second and third mold blocks. Each of the mold blocks has a plurality of cavities formed therein. The cavities formed in the first mold block are designed to mate with the cavities formed in the second and third mold blocks when the stack mold is closed to form a plurality of arcuately-shaped cavities. The stack mold further contains a pair of slide carriers movably connected to each of the second and third mold blocks and a plurality of inner cores secured to each of the slide carriers.

The stack mold is closed by first moving both of the pairs of slide carriers such that each of the inner cores is positioned within one of the arcuately-shaped cavities in the first mold block to form a hollow interior in each of the molded articles. The first and second mold blocks are then moved against the third mold block. Molten material is introduced into the arcuately-shaped cavities and is allowed to solidify. The stack mold is then opened by moving the first and second mold blocks away from the third mold block and then moving both of the pairs of slide carriers outward to remove the inner cores from the arcuately-shaped cavities. The injection molded articles can then be removed from the stack mold.

The general object of this invention is to provide a process for injection molding arcuately-shaped articles. A more specific object of this invention is to provide a process for injection molding an arcuately-shaped outer tube which can be assembled with an inner tube to form a curved tampon applicator.

Another object of this invention is to provide an efficient process for injection molding arcuately-shaped, hollow articles.

A further object of this invention is to provide a process for injection molding curved outer tubes quickly and inexpensively.

Still another object of this invention is to provide a process for injection molding arcuately-shaped, hollow articles having relatively thin side walls.

Still further, an object of this invention is to provide a process for injection molding arcuately-shaped, hollow articles in a stack mold.

Other objects and advantages of the present invention will become more apparent to those skilled in the art in view of the following description and the accompanying drawings.

DETAILED DESCRIPTION OF THE PREFERRED EMBODIMENT

Figure 1:
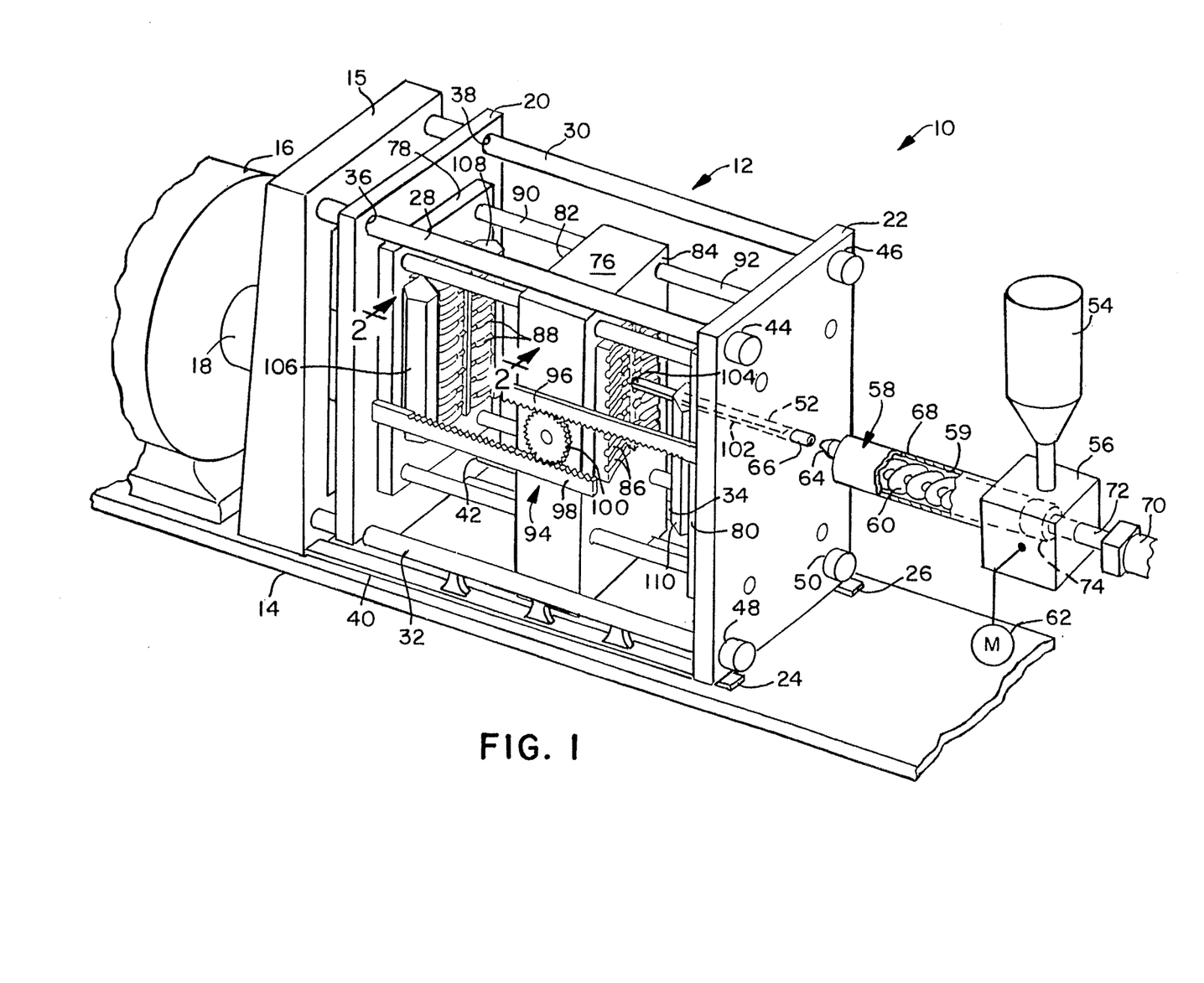
FIG. 1 is a perspective view of an injection molding machine having a stack mold positioned therein and shown in an open position.

Referring to FIG. 1, an injection molding machine 10 is shown having a stack mold 12 positioned therein. For purposes of discussion, the injection molding machine 10 is capable of molding articles out of thermoplastic or synthetic resins, such as plastic. Polyethylene and polypropylene are two plastic materials which can be injection molded.

The injection molding machine 10 includes a base 14 which supports a hydraulic cylinder 16. The hydraulic cylinder 16 is capable of moving a piston rod 18 back and forth in a reciprocal fashion and at very high pressures. It should be noted that the hydraulic cylinder 16 could be replaced with two or more smaller cylinders if desired which would each have a reciprocally movable piston rod. The injection molding machine 10 can exert a tremendous amount of pressure between first and second platens, 20 and 22 respectively. Injection molding machines are typically rated in tons of pressure which can be applied. For example, injection molding machines are commercially available in various sizes with some machines capable of supplying about 15 to about 2,000 tons of pressure. The amount of pressure needed will depend upon the size of mold which is utilized, the size and shape of the finished article, the material from which it is molded, the cycle time, etc. For injection molding an arcuately-shaped, hollow article which can be used as the outer tube of a tampon applicator, an injection molding machine capable of delivering pressures above 200 tons is acceptable for a thirty-two cavity mold. An injection molding machine in the 200 to 400 ton range is preferable, for it can operate more efficiently than a smaller machine and may be able to handle a larger cavity mold.

Secured to the free end of the piston rod 18 is a first movable platen 20. A platen is a flat member or plate having a plurality of bolt holes formed therethrough which facilitates mounting a mold block to it. The first platen 20 will move to the right or left along with the piston rod 18.

A second platen 22 is also present in the injection molding machine 10. The second platen 22 is aligned parallel to the first platen 20 and is spaced apart therefrom. The second platen 22 is a stationary member. The second platen 22 is supported by a pair of tie bars 32 and 34 which in turn are supported by a pair of support rails 24 and 26. The support rails 24 and 26 can be secured to the base 14. The tie bars 32 and 34 also provide stability and a surface onto which the first platen 20 can slide. The first platen 20 can be provided with rollers (not shown) or some other type of mechanism to allow it to be movable on the tie bars 32 and 34.

The two tie bars 32 and 34 cooperate with two additional tie bars 28 and 30 to hold the platens in alignment with one another. The four tie bars 28, 30, 32 and 34 pass through openings 36, 38, 40 and 42, respectively formed adjacent to each corner of the first platen 20 and through openings 44, 46, 48 and 50, respectively, formed adjacent to each corner of the second platen 22. The tie bars 28, 30, 32 and 34 pass completely through both the first and second platens 20 and 22 and extend to the left of the first platen 20 a sufficient length to allow for the maximum amount of travel which the first platen 20 can experience. The four tie bars 28, 30, 32 and 34 are supported by the vertical frame member 15 in addition to the two support rails 24 and 26. The four tie bars 28, 30, 32 and 34 provide support and alignment to the first and second platens 20 and 22. The second platen 22 also has an axial opening 52 formed therethrough, the purpose of which will be explained shortly.

The stack mold 12 is positioned between the first and second platens 20 and 22. The specific construction of the stack mold 12 will be explained below.

The injection molding machine 10 also contains one or more hoppers 54 which can hold a large quantity of solid pellets from which the finished arcuately-shaped articles can be molded. Various types of synthetic and thermoplastic resins, and blends thereof, can be used. Linear low density polyethylene pellets are preferred because this material is readily available, relatively inexpensive and can be easily injection molded. Linear low density polyethylene is commercially available from The Dow Chemical Company having an office located at 1676 North California Blvd., Walnut Creek, Calif. Linear low density polyethylene sold under code name Dowlex #2503 works well. The pellets are small in size, usually less than ¼ inch in diameter. It should be noted that the pellets can have almost any geometrical shape. Spherical and cylindrical shaped pellets are the most common. Although only one hopper 54 is shown in FIG. 1, additional hoppers can be present to hold other pellets which can be combined with the polyethylene pellets. For example, a colorant or whitener may be added to the molded articles to increase their aesthetic appearance. Colorants are commercially available from Ampacet Corporation having an office located at 660 White Plains Road Tarrytown, N.Y. 10591. A preferred whitener when molding tampon applicators is titanium dioxide ($TiO_2$). In addition, a slip agent may be added to facilitate removal of the finished articles from the mold blocks. A suitable slip agent is "Kemimide E" available from Witco-Humko Corporation having an office located at 10100 Santa Monica Blvd., Los Angles, Calif. 90067.

The thermoplastic or synthetic resin pellets can be clear or opaque. For some products, the material should be water dispersible and/or water soluble. For tampon applicators, it is desirable for the thermoplastic material to be photodegradable, ultraviolet light degradable, biodegradable or compostable. The finished arcuately-shaped outer tubes of a tampon applicator should be flushable in conventional toilet systems and be capable of breaking apart in water maintained below, at or above room temperature.

It should also be noted that it is possible to mix two or more different kinds of synthetic or thermoplastic resins together in order to obtain a unique kind of plastic. For example, if one desired to mold an article that was water dispersible, one may need to mix two distinct kinds of materials each retained in separate hoppers 54.

The pellets contained in the hopper(s) 54 are routed to a feed mechanism 56 where they are combined in a predetermined amount. The feed mechanism 56 includes a cylindrical barrel 58 having an elongated passageway 59 formed therein. Positioned in the passageway 59 is a reciprocating auger type feed screw 60. The feed screw 60 is also capable of being intermittently rotated so as to turn the auger. A motor 62, connected by one of many known linkage mechanisms, supplies the rotary motion to the feed screw 60. The feed screw 60 has a conical tip 64 formed on its opposite end which is axially aligned with the opening 52 formed in the second platen 22. The tip 64 of the feed screw 60 is designed to be inserted into an end of a hollow sprue bar 66. The sprue bar 66 is movably positioned within the opening 52 and is secured to the center section of the stack mold 12. The exact point of attachment of the sprue bar and it's function will be explained below.

Surrounding the periphery of the feed screw 60 is a heater 68 which can elevate the temperature of the plastic pellets as they are transported toward the conical tip 64. As the solid pellets are moved forward by the feed screw 60, they are heated to a temperature approaching, equal to or above their melting temperature. The elevated temperature causes the solid pellets to melt and turn into molten fluid which can flow through the conical tip 64 of the feed screw 60 and into the sprue bar 66. The exact temperature to which the plastic pellets are heated will depend upon the melting point of the specific synthetic or thermoplastic resins being used. The temperature will also depend upon the length of time over which the material is heated, the speed of the feed screw 60, the quantity of material being heated, the type of heater used, etc. Under no circumstances should the material be allowed to burn for this would prevent the material from flowing into the stack mold 12.

For linear low density polyethylene, a temperature range for the barrel 58 of about 300° F. to about 550° F. range is acceptable. A more preferred temperature range for linear low density polyethylene in the barrel 58 is about 330° F. to about 390° F., and a most preferred temperature range in the barrel 58 is about 350° F. to about 380° F.

The injection molding machine 10 further includes a hydraulic cylinder 70 having an elongated piston rod 72 extending outward therefrom. A piston 74 is secured to an end of the piston rod 72 and in turn is connected to an end of the feed screw 60. The piston 74 is movable in a reciprocal fashion and is capable of pushing the feed screw 60 to the left within the barrel 58, as shown. Movement of the piston 74 to the left will deliver a predetermined quantity of molten plastic from the feed screw 60 to the sprue bar 66 at a pressure in the range of between about 200 psi to about 2,500 psi. A pressure of about 1,400 psi is preferred for molding arcuately-shaped hollow tubes useful as part of a tampon applicator when a thirty-two cavity mold is utilized. The piston 74 will return to the right on it's return stroke under the influence of a build up of molten material behind the conical tip 64. As new material is introduced into the feed mechanism 56, the motor 62 rotates the auger type feed screw 60 and molten material is moved forward toward the conical tip 64. The molten material displaces the piston 74 to the right as it accumulates behind the conical tip 64.

The stack mold 12 is positioned between the first and second platens 20 and 22. The stack mold 12 includes first, second and third mold blocks, 76, 78 and 80 respectively. The first or center mold block 76 is positioned between the second and third mold blocks 78 and 80. The first mold block 76 is moveable and has two oppositely aligned surfaces 82 and 84. Each of the surfaces 82 and 84 has a plurality of cavities 86 formed therein. When an arcuately-shaped article is to be molded, each of the cavities 86 will have a curved or arcuate shape. The second mold block 78 is secured to the first platen 20 and is movable with it. The third mold block 80 is secured to the second platen 22 and is therefore stationary. Bolts and clamps can be used to secure and position the second and third mold blocks 78 and 80 in a desired position. Each of the second and third mold blocks 78 and 80 also have a plurality of cavities 88 formed therein. The cavities 88 are designed to line up and mate with the cavities 86 formed in the first mold block 76 when the stack mold 12 is closed. The size, depth and shape of the cavities 86 and 88 are designed to provide a female impression of the outer profile of the finished injection molded article. The cavities 86 and 88 can have a high polished finish.

For molding an arcuately-shaped outer tube for a tampon applicator, it is advantageous to form an even number of cavities in each surface 82 and 84 of the first mold block 76 and in the second and third mold blocks 78 and 80. For good results sixteen or thirty-two cavities 86 can be formed in each surface 82 and 84 of the first mold block 76. An equal number of cavities 88 can be formed in the second and third mold blocks 78 and 80. When sixteen cavities 88 are present in each of the second and third mold blocks 78 and 80, a total of thirty-two articles can be injection molded during each cycle of the injection molding machine 10. If thirty-two cavities 88 are present in each of the second and third mold blocks 78 and 80, a total of sixty-four articles could be injection molded during each cycle of the injection molding machine 10. Therefore, it should be apparent that the use of a mold block having a greater number of cavities will provide a larger quantity of finished articles per cycle.

The first mold block 76 also contain four leader pins 90 secured adjacent to each corner which extend outward toward the second mold block 78 and another four leader pins 92 secured adjacent to each corner which extend outward toward the third mold block 80. The leader pin 90 and 92 are received in bushings positioned in each of the second and third mold blocks 78 and 80. The leader pin 90 and 92 provide a physical connection between the three blocks 76, 78 and 80 of the stack mold 12 and assist in assuring that the cavities 86 and 88 are kept in axial alignment.

The first mold block 76 further contains a rack and pinion mechanism 94 for the interconversion of rotary and linear motion. The mechanism 94 includes a first rack 96, a second rack 98 and a pinion 100. The first rack 96 is slidable at one end to the first mold block 76 and is securely affixed at an opposite end to the third mold block 80. The second rack 98 is also slidable at one end to the first mold block 76 and is securely affixed at an opposite end to the third mold block 80. The rack and pinion mechanism 94 will allow the second mold block 78 to move toward or away from the first mold block 76 a distance equal to the distance the first mold block 76 moves toward or away from the third mold block 80. The second mold block 78 will simultaneously move toward or away from the first mold block 76 as the first mold block 76 moves toward or away from the third mold block 80. The second mold block 78 will actually travel twice as far as the first mold block 76 in the same amount of time. The rack and pinion mechanism 94 permits the three mold blocks 76, 78 and 80 to be opened and closed in a very short period of time. This is important because if one can shorten the time needed to open and close the stack mold 12, one can shorten the cycle time required to mold the articles.

As stated above, a hollow sprue bar 66 is position in the opening 52 formed in the second platen 22. The third mold block 80 contains a similarly sized opening 102 which is axially aligned with the opening 52. The sprue bar 66 passes through both of these openings 52 and 102 and engages with an opening 104 formed in the center of the surface 84 of the first mold block 76. The sprue bar 66 is affixed to the first mold block 76 and will move with it. The sprue bar 66 has sufficient length extending to the right of the second platen 22 such that a portion of it is always positioned within the opening 52. The sprue bar 66 contains electric heating elements so as to keep any plastic material present therein in a molten state. The sprue bar 66 moves to the right as the first mold block 76 is pushed against the third mold block 80. This permits the sprue bar 66 to engage the conical tip 64 and a continuous passage for the molten plastic material will be formed when the feed screw 60 is pushed to the left by the piston 74. The molten plastic material is then metered out of a chamber situated to the right of the conical tip 64 and is forced into the sprue bar 66. This action will cause an equal amount of molten plastic material present in the sprue bar 66 to be injected into the central opening 104 formed in the first mold block 76.

The molten plastic material is injected under pressure when the stack mold 12 is in a closed position. In the closed position, the cavities 88 formed in the second and third mold blocks, 78 and 80 respectively, will line up with the cavities 86 formed in the first mold block 76. The mating of the cavities 86 and 88 form arcuately-shaped mold cavities which will resemble the outer configuration of the finished molded article. This means that as the molten plastic material enters the cavities 86 and 88, it will fill them up completely.

The molten plastic material is routed from the central opening 104 through a multitude of small diameter passageways constructed in the first mold block 76 to the void areas formed by the mating cavities 86 and 88. The formation of such passageways within the stack mold 12 is known to those skilled in building stack molds for injection molding machines. The stack mold 12 is heated and the routing of the molten plastic material to the various cavities 86 is typically referred to as a hot runner system by those skilled in the molding art.

Figure 2:
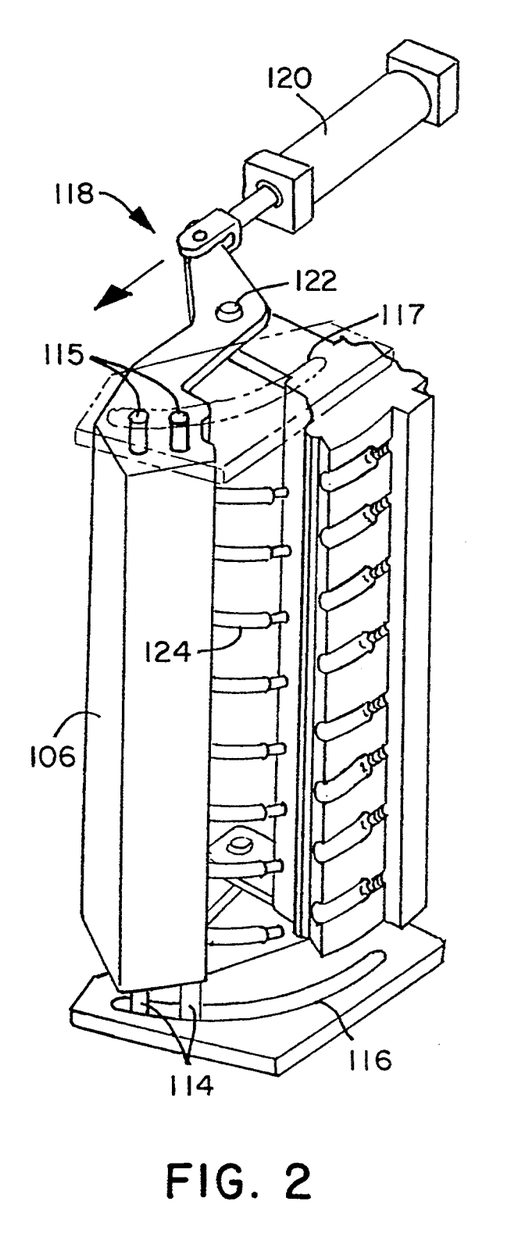
FIG. 2 is a partial view of the stack mold taken along line 2—2 of FIG. 1 showing a slide carrier with eight inner cores designed to mate with the mold cavities formed in the second mold block.

Referring to FIGS. 1 and 2, the stack mold 12 further includes a first pair of slide carriers 106 and 108 movably connected to the second mold block 78 and a second pair of slide carriers 110 and 112 connected to the third mold block 80. Slide carrier 112 is not shown in FIG. 1 due to the angle of the perspective view. Each slide carrier 106, 108, 110 and 112 has a pair of pins 114 formed on a lower surface thereof and a pair of pins 115 formed on an upper surface thereof. Each pair of pins 114 and 115 are equipped with a roller bearing (not shown) and the pins 114 and 115 are movably retained in arcuate grooves 116 and 117. The pins 114 and 115 can move in the corresponding grooves 116 and 117 along an arcuate path through an angle of from about 10 degrees to about 90 degrees, preferably through an angle of from about 15 degrees to about 45 degrees, and most preferably, through an angle of about 30 degrees. The exact angle will depend on how much travel is needed to move each of the slide carriers 106, 108, 110 and 112 relative to the second and third mold blocks, 78 and 80 respectively.

Each slide carrier 106, 108, 110 and 112 also contains a linkage mechanism 118 which is attached between an actuator 120 and a pin 122 located on the upper surface of the second or third mold block 78 and 80. The actuator 120 can be a hydraulic cylinder. Alternatively, the actuator 120 could be a pneumatic cylinder, an electrically activate cylinder or be a mechanical device, such as motor, a cam, etc.

Each slide carrier 106, 108, 110 and 112 contains a plurality of elongated inner cores 124 which are secured in place by tapered interlocks. Each inner core 124 has an arcuate shape which matches the inner configuration of each of the finished molded articles. The inner core should have a vapor-hone finish or a draw polished surface to prevent the plastic from sticking to it. If a draw polish finish is utilized, the draw should be in the same direction as the direction in which the inner core travels to be withdrawn from the arcuately-shaped cavity. When each of the second and third mold blocks, 78 and 80 respectively, contain sixteen cavities 88, each slide carrier 106, 108, 110 and 112 will have eight inner cores 124 secured to it. Preferably, the cavities 88 are arranged in two vertical rows in the second and third mold blocks 78 and 80. Each of the slide carrier 106, 108, 110 and 112 will contain eight inner cores 124 arranged vertically to line up with one of the two rows of cavities 88 formed in each of the second and third mold blocks, 78 and 80 respectively. Each inner core 124 is capable of being positioned within one of the arcuately-shaped cavities 86 to form the hollow interior in the finished injection molded article.

When the actuators 120 are initially activated, they will cause the linkage mechanisms 118 to move each slide carrier 106, 108, 110 and 112 via the pins 114 and 115 alone the arcuate paths 116 and 117. This enables each slide carrier 106, 108, 110 and 112 to move inward toward the vertical centerline of both the second and third mold blocks, 78 and 80 respectively. This action positions each of the inner cores 124 in registration with one of the cavities 88. This positioning is referred to as a "single pull" and differs from a "double pull" wherein it is necessary to have two mating members in order to form the inner core. A "single pull" is instrumental in allowing the stack mold 12 to operate economically since a greater number of cavities 88 per mold block 76, 78 and 80 can be present. The "single pull" design also uses fewer moving parts although it is more intricate.

The first and second mold blocks, 76 and 78 respectively, are moved to their closed position after the slide carriers 106, 108, 110 and 112 have moved inward. The first and second mold blocks, 76 and 78 respectively, will close simultaneous by the action of the rack and pinion mechanism 94. When the stack mold 12 is closed, the second surface 84 of the first mold block 76 will contact the third mold block 80 and the second mold block 78 will contact the first surface of the first mold block 76. In simple terms, all three blocks 76, 78 and 80 are brought together and are physically touching.

PROCESS

Figure 3:
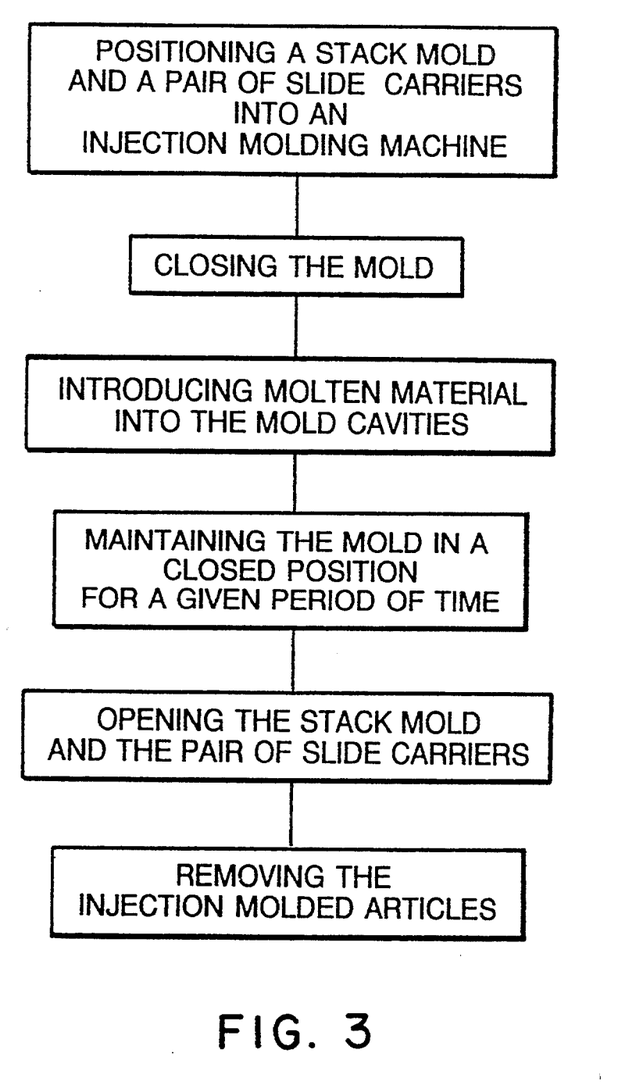
FIG. 3 is a flow diagram of the process for injection molding arcuately-shaped hollow articles.

Referring to FIG. 3, the process for injection molding arcuately-shaped hollow articles will now be described. The process will be described starting with the stack mold 12 in the closed position, located between the first and second platens, 20 and 22 respectively. Molten material is introduced at a very high pressure to the arcuately-shaped cavities 88 formed by the stack mold 12. The pressure used to push the molten material through the various passageways and into the mold cavities 88 can range from between about 1,000 to about 2,000 psi, preferably about 1,400 psi. This force is generated by the action of the hydraulic cylinder 70, piston rod 72 and piston 74 which expels the molten material out of the conical tip 64 of the feed screw 60 by pushing the auger forward or to the left, as depicted in FIG. 1. A predetermined quantity of the molten material, retained at the forward end of the auger, is injected into the sprue bar 66 with each stroke of the piston 74. The molten material enters the heated sprue bar 66 and will force molten material already present in the sprue bar 66 to move forward through the opening 104 formed in the first mold block 76. This action assures that a predetermined quantity of molten material will be routed to the first mold block 76 on each stroke of the piston 74 and the feed screw 60.

The exact amount of molten material which is needed has to be calculated ahead of time. The calculation will vary depending on the size of the mold cavities 88, the number of cavities 88, the amount of material needed to fill each cavity 88, the length and diameters of the passageways between the opening 104 and each of the cavities 88, etc. The quantity of molten material required to fill all of the cavities 88 is then factored into the size and diameter of the feed screw 60 and the stroke of the piston 74. The feed mechanism 56 and the hydraulic cylinder 70 can then be adjusted and controlled by a computer to assure that the correct amount of molten material is being supplied for each cycle of the stack mold 12. The computer can also control and maintain the stack mold 12 at an optimal temperature and feed the molten material into the stack mold 12 at precisely the right time.

Once the molten material is in the cavities 88, the temperature of the stack mold 12 can be regulated to minimize the time it takes to allow the molten material to solidify. The word "regulated" is used to mean that the temperature of the stack mold 12 can be maintained at a constant temperature or the temperature can actually be decreased, such as by cooling the mold, to allow the molten material to solidify quicker. It has been found that by maintaining the temperature of the stack mold 12 at about 90° F., the molten material can solidify in a few seconds.

For linear low density polyethylene, the time required to solidify the molten material is relatively short, for example, about 3 to about 10 seconds, and preferably, less than about 5 seconds. The cooling time should be kept as short as possible. It should be remembered that the size and shape of the finished molded articles, the temperature of the stack mold 12, the temperature of the molten material, among other parameters, will all influence the cooling time. It should also be noted that the stack mold 12 can contain cooling passages which can route a coolant, such as cold water, throughout the mold block 76 to decrease the time it takes for the molten material to solidify.

After the material has solidified, the stack mold 12 is opened by moving the first and second mold blocks, 76 and 78 respectively, away from the third mold block 80. The first and second mold blocks, 76 and 78 respectively, will move simultaneously via the action of the rack and pinion mechanism 94. After the first and second mold blocks 76 and 78 have opened a predetermined amount of about 5.1 inches (130 mm), the slide carriers 106, 108, 110 and 112 can be actuated by the actuators 120 to move outward away from the second and third mold blocks. In other words, the slide carriers 106, 108, 110 and 112 simultaneously open with the first and second mold blocks 76 and 78 after the first and second mold blocks 76 and 78 have started to move away from the third mold block 80. This simultaneous movement of both the first and second mold blocks 76 and 78 along with the slide carriers 106, 108, 110 and 112 will decrease the amount of time required to open the stack mold 12. It should be noted that if time is not of the essence, the slide carriers 106, 108, 110 and 112 can open after the first and second mold blocks 76 and 78 are completely open. As the slide carriers 106, 108, 110 and 112 are moved outward, the inner cores 124 will be simultaneously withdrawn from the molded articles. This "single pull" feature enhances a short cycle time.

The molded articles will be retained in the mold cavities 88 formed in the second and third mold blocks 78 and 80. Knock out pins (not shown) but which are movably retained in the second and third mold blocks, 78 and 80 respectively, can then be used to separate the finished molded articles from the mold cavities. For some designs, the finished articles may be capable of falling out of the mold cavities 88 by themselves and therefore there would be no need to use knock out pins. However, when a pick off mechanism is used to extract the finished articles from the injection molding machine 10, it is advisable to use knock out pins to assure that all of the molded articles are removed before the stack mold 12 is allowed to close for the next cycle.

The entire cycle time for the stack mold 12 to go through one complete cycle should be less than 20 seconds, preferably less than about 17 seconds, and most preferably, less than about 15 seconds. This will assist in lowering the cost of the finished molded article. The complete cycle involves closing the stack mold 12, injecting molten material to each of the mold cavities, allowing the molting material to solidify, opening the stack mold and removing the finished articles. For this cycle, the stack mold 12 should be kept in the closed position from about 3 to about 8 seconds.

Figure 4:
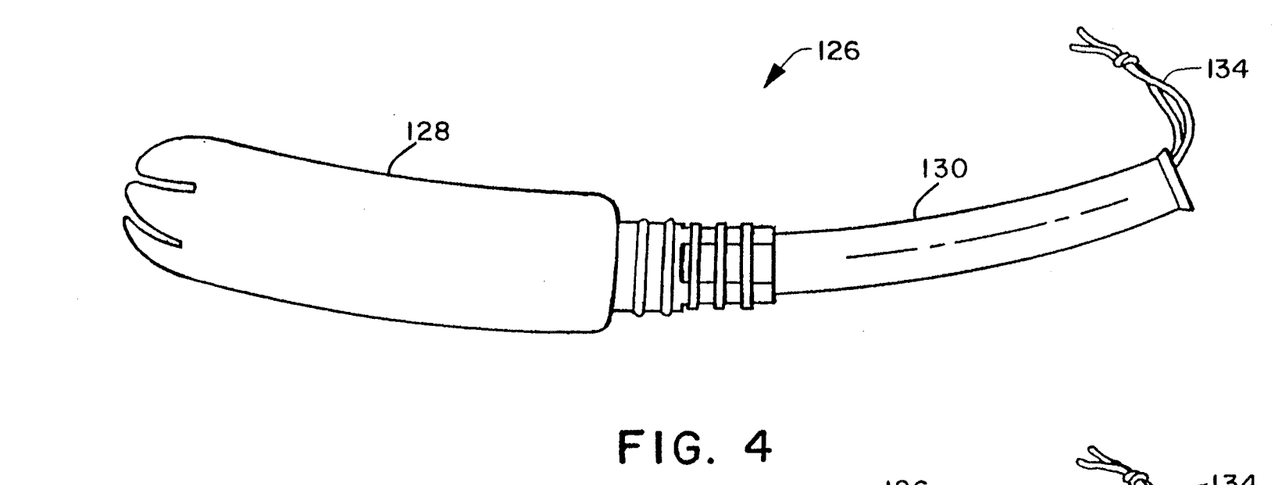
FIG. 4 is a side elevation view of a curved tampon applicator consisting of an outer tube and inner tube telescopically assembled.
Figure 5:
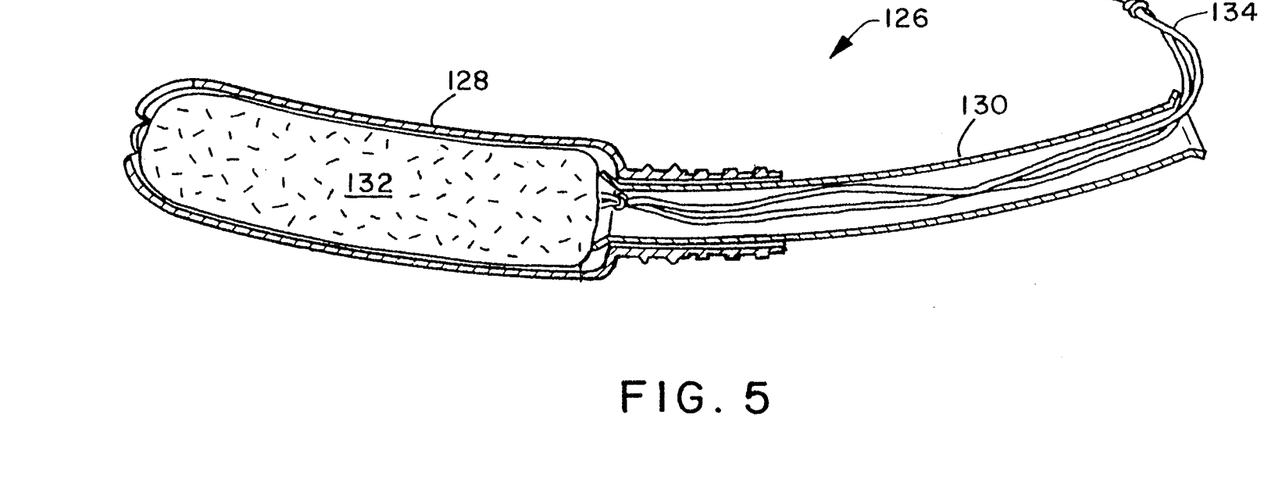
FIG. 5 is a cross-sectional view of the curved tampon applicator shown in FIG. 4 depicting a catamenial tampon housed in the outer tube.

Referring to FIGS. 4 and 5, an arcuately-shaped tampon applicator 126 is shown consisting of an arcuately-shaped, hollow outer tube 128 and an arcuately-shaped, hollow inner tube 130. The two tubes 128 and 130 are telescopically assembled. An absorbent tampon 132 is housed in the enlarged outer tube 128 and can be inserted into a woman's vagina by pushing the inner tube 130 into the outer tube 128. After the tampon 132 has been inserted into the woman's vagina, the applicator 126 can be disposed of. A withdrawal string 134 is secured to the tampon 132 and provides a means for removing the tampon 132 from the woman's vagina after it has accumulated body fluid. U.S. Pat. No. 5,267,953 issued Dec. 7, 1993 to Paul et al. describes the working of a curved tampon applicator and is incorporated herein by reference and made a part hereof.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A process for injection molding arcuately-shaped hollow articles, said process comprising the steps of:
   a) positioning a stack mold into an injection molding machine, said stack mold including first, second and third mold blocks with said first mold block positioned between said second and third mold blocks, each of said mold blocks having a plurality of cavities formed therein, said cavities formed in said first mold block mating with said cavities formed in said second and third mold blocks when said stack mold is closed to form a plurality of arcuately-shaped cavities, said stack mold further having a pair of slide carriers movably connected to each of said second and third mold blocks and a plurality of inner cores secured to each of said slide carriers;

b) closing said stack mold by first moving both of said pairs of slide carriers such that each of said inner cores is positioned within one of said cavities formed in said second and third mold blocks to form a hollow interior in each of said molded articles, and then moving said first and second mold blocks against said third mold block;

c) introducing molten material into said arcuately-shaped cavities and allowing said material to solidify; and d) opening said stack mold by moving said first and second mold blocks away from said third mold block and moving both of said pairs of slide carriers outward away from said arcuately-shaped cavities.

2. The process of claim 1 wherein both of said pairs of slide carriers are movable along an arcuate path.

3. The process of claim 2 wherein each slide carrier is movable along said arcuate path through an angle of from about 10 degrees to about 90 degrees.

4. The process of claim 1 wherein each slide carrier moves away from said second and third mold blocks after said first and second mold blocks have started to move away from said third mold block.

5. The process of claim 1 wherein each of said slide carriers is hydraulically actuated.

6. The process of claim 1 wherein said stack mold is kept in the closed position from about 3 seconds to about 8 seconds.

7. The process of claim 1 wherein said stack mold has a cycle time of less than about 20 seconds.

8. The process of claim 1 wherein said stack mold has a cycle time of less than about 15 seconds.

9. The process of claim 1 wherein said stack mold is operated at a temperature of about 90° F.

10. A process for injection molding arcuately-shaped hollow articles, said process comprising the steps of:

a) positioning a stack mold into an injection molding machine, said stack mold including first, second and third mold blocks with said first mold block positioned between said second and third mold blocks, each of said mold blocks having a plurality of cavities formed therein, said cavities formed in said first mold block mating with said cavities formed in said second and third mold blocks when said stack mold is closed to form a plurality of arcuately-shaped cavities, said stack mold further having a pair of slide carriers movably connected to each of said second and third mold blocks and a plurality of inner cores secured to each of said slide carriers, each of said inner cores capable of being positioned within one of said arcuately-shaped cavities to form a hollow interior in said injection molded articles;

b) closing said stack mold by first moving both of said pairs of slide carriers along an arcuate path such that each of said inner cores is positioned within one of said cavities formed in said second and third mold blocks and moving said first and second mold blocks against said third mold block;

c) introducing molten material into said arcuately-shaped cavities and allowing said material to solidify;

d) opening said stack mold by moving said first and second mold blocks away from said third mold block and moving both of said pairs of slide carriers along said arcuate paths such that said inner cores are removed from said arcuately-shaped cavities; and e) removing said injection molded articles from said second and third mold blocks.

11. The process of claim 10 wherein each slide carrier is movable along an arcuate path through an angle of from about 10 degrees to about 90 degrees.

12. The process of claim 10 wherein each slide carrier moves away from said second and third mold blocks after said first and second mold blocks have started to move away from said third mold block.

13. The process of claim 10 wherein molten material is introduced into said stack mold at a pressure of between about 1,000 psi to about 2,000 psi.

14. The process of claim 13 wherein molten material is introduced into said stack mold at a pressure of about 1,400 psi.

15. The process of claim 10 wherein said molten material is plastic.

16. A process for injection molding arcuately-shaped hollow articles, said process comprising the steps of:

a) positioning a stack mold into an injection molding machine, said stack mold including first, second and third mold blocks with said first mold block positioned between said second and third mold blocks, each of said mold blocks having a plurality of cavities formed therein, said cavities formed in said first mold block mating with said cavities formed in said second and third mold blocks when said stack mold is closed to form a plurality of arcuately-shaped cavities, said stack mold further having a pair of slide carriers movably connected to each of said second and third mold blocks, and a plurality of inner cores secured to each of said slide carriers, each of said inner cores capable of being positioned within one of said arcuately-shaped cavities to form a hollow interior in said injection molded articles;

b) closing said stack mold by first moving both of said pairs of slide carriers along an arcuate path such that each of said inner cores is positioned within one of said cavities formed in said second and third mold blocks and then moving said first and second mold blocks against said third mold block;

c) introducing molten material into said cavities and allowing said material to solidify;

d) maintaining said stack mold in a closed position for a predetermined period of time;

e) opening said stack mold by moving said first and second mold blocks away from said third mold block and moving both of said pairs of slide carriers along said arcuate paths such that said inner cores are removed from said arcuately-shaped cavities; and f) removing said injection molded articles from said second and third mold blocks.

17. The process of claim 16 wherein each of said slide carriers is hydraulically actuated.

18. The process of claim 16 wherein said stack mold has a cycle time of less than 20 seconds.

19. The process of claim 16 wherein said stack mold is operated at a temperature of about 90° F.

20. The process of claim 16 wherein molten material is introduced into said stack mold at a pressure of about 1,400 psi.

* * * * *